United States Patent [19]
Rottenberg et al.

[11] Patent Number: 6,007,479
[45] Date of Patent: Dec. 28, 1999

[54] HEART ASSIST SYSTEM AND METHOD

[75] Inventors: Dan Rottenberg, Haifa; Dudu Haimovich, Ramat Ishai, both of Israel

[73] Assignee: H.D.S. Systems Ltd., Upper Yoqneam, Israel

[21] Appl. No.: 08/983,611

[22] PCT Filed: Jul. 8, 1996

[86] PCT No.: PCT/IL96/00045

§ 371 Date: Dec. 31, 1997

§ 102(e) Date: Dec. 31, 1997

[87] PCT Pub. No.: WO97/02850

PCT Pub. Date: Jan. 30, 1997

[51] Int. Cl.[6] ......................................... A61M 1/12
[52] U.S. Cl. ............................................... 600/16
[58] Field of Search ................... 600/16, 17, 18

[56] References Cited

U.S. PATENT DOCUMENTS

| | | |
|---|---|---|
| 3,592,184 | 7/1971 | Watkins et al. . |
| 3,974,825 | 8/1976 | Normann ................................ 600/17 |
| 3,995,617 | 12/1976 | Watkins et al. ......................... 600/16 |
| 4,357,959 | 11/1982 | Shetler . |
| 4,906,229 | 3/1990 | Wampler . |
| 5,169,385 | 12/1992 | Turnbull . |
| 5,263,979 | 11/1993 | Isoyama et al. ........................ 600/17 |

FOREIGN PATENT DOCUMENTS

| | | |
|---|---|---|
| 1370546 | 10/1974 | United Kingdom . |
| 90/09204 | 8/1990 | WIPO . |

*Primary Examiner*—William E. Kamm
*Attorney, Agent, or Firm*—Fenster & Company Patent Attorneys, Ltd.

[57] ABSTRACT

A cardiac assist device includes a cannula with intake and outflow valve in the distal end portion is positioned in a bloodstream. A diaphragm in the proximal portion of the cannula, powered by external pressure-producing mechanism, forms a reservoir to exert pressure on the cannula volume at the valves to effect blood flow assistance to the patient's heart.

29 Claims, 8 Drawing Sheets

HEART ASSIST SYSTEM AND METHOD

FIELD OF THE INVENTION

The present invention relates generally to devices and systems for augmenting cardiac output, and specifically to intra-ventricular cardiac assist pumps.

BACKGROUND OF THE INVENTION

Intra-aortic and intra-ventricular cardiac assist devices are well known in the art. These devices are generally used to reduce the heart's work load after insult or surgery. They may also be used to increase blood flow from the left ventricle of the heart into the aorta in cases of insufficient cardiac output due, for example, to acute or chronic heart ailments or to interference with normal cardiac function during surgery.

One of the best-known and most widely-used intra-aortic pump systems is the Intra-Aortic Balloon Pump (IABP), comprising a catheter, having an inflatable balloon at its distal end, which is inserted through an artery into the aorta. The balloon is then alternately inflated and deflated by an external pump drive, so as to alternately block and unblock blood flow through the aorta, in synchrony with the beating of the heart, in order to assist the left ventricle in propelling blood into the arterial system. The IABP, however, provides only limited augmentation of the heart's natural, unassisted output, and is not adequate for overcoming heart failure.

U.S. Pat. No. 4,014,317, which is incorporated herein by reference, describes a cardiocirculatory assist cannula with a balloon pump and cardiac pacing electrode. The cannula is inserted percutaneously through the aorta so that its distal end is inside the left ventricle of the heart. During systole, inlet valves on the cannula inside the left ventricle open, and the contraction of the ventricle forces blood to flow into the cannula. Then, during diastole, the blood flows out. into the aorta, through one or more outlet valves along the cannula downstream from the inlet valve. A gas-filled balloon, similar in function to the IABP described above, is connected to the cannula downstream of the outlet valves. The balloon is typically inflated during diastole and deflated during systole, to assist in perfusion of the coronary arteries. The cannula has a small stroke volume, however, and relies on the contractile force of the heart to pump the blood. It is therefore of limited usefulness in augmenting the blood output of a weakened or failing heart.

U.S. Pat. No. 4,906,229, which is also incorporated herein by reference, describes a high-frequency transvaivular axisymmetric blood pump. The pump includes a small internal volume, which may be alternately expanded and reduced by pneumatic or hydraulic pressure which is exerted via a flexible membrane radially surrounding the volume. The volume has intake and outlet ends, with one-way axial valves at both of the ends, so that blood can flow only from the heart into the aorta. The pump is connected via the one-way intake valve to a cannula, which is inserted into the left ventricle of the heart through the aortic valve. When the internal volume is expanded, blood flows into the pump from the ventricle. The volume is then reduced, and the blood is ejected into the aorta through the outlet end. This pump is designed to operate at a frequency of 600 to 1,000 cycles per minute. Since the stroke volume of the pump is typically only about 3–5 cc, these high cycle rates are needed in order to provide adequate perfusion.

In the Hemopump Cardiac Assist System, distributed by Johnson & Johnson Interventional Systems, a cannula containing a special, miniature rotor pump mechani,n is inserted into the aorta. The pump is driven by a drive unit outside the body, to pump blood continuously from the aorta into the rest of the arterial system, thereby supplementing the heart's natural output rate. A system of this type is similarly described in U.S. Pat. No. 5,092,844, which is incorporated herein by reference. While continuous-flow devices are useful for short-term augmentation ot cardiac output, it is believed that pulsatile pumps provide more effective long-term support, since they approximate more closely the natural pump action of the heart.

SUMMARY OF THE INVENTION

It is an object of the present invention to provide an intraventricular cardiac assist pump having a sufficiently large internal volume and improved valve structure, so that adequate pulsatile perfiusion of the body may be dependably maintained.

In one aspect of the present invention, wherein the pump comprises a cannula, one-way valve structures are provided in the sides of the cannula so as to reliably control the alternate inflow and outflow of blood therefrom.

In preferred embodiments of the present invention, an intraventricular cardiac assist pump comprises a cannula, whose distal end is inserted through the aorta into the left ventricle, and a pulsatile drive unit, coupled to the cannula at the proximal end thereof The cannula comprises an outer sheath, defining and enclosing an internal lumen, having at least one intake valve, adjacent to the cannula's distal end, and one or more outlet valves, disposed radially along the length of the cannula downstream from the intake valve. The pulsatile drive unit alternately reduces and increases the fluid pressure in the cannula. When the pressure is reduced, the at least one intake valve opens, while the one or more outlet vaives are closed, and blood flows through the intake valve into the lumen of the cannula. The pressure in the cannula is then increased, causing the intake valve to close and the outlet valves to open, so that blood flows out of the lumen into the aorta.

In some preferred embodiments of the present invention, the pulsatile drive unit includes a fluid reservoir, comprising first and second chambers, separated by a flexible diaphragm, each chamber having a fluid port. The fluid port of the first chamber is connected to the proximal end of the cannula, so that blood may flow between the chamber and the cannula. The fluid port of the second chamber is connected to a hydraulic drive, which alternately increases and decreases the pressure, and hence the volume, of a control fluid in the second chamber. The flexible diaphragm couples pressure changes from the second to the first chamber, without direct contact between the fluid in the second chamber and the blood in the first chamber, thereby controlling the flow of blood into and out of the lumen of the cannula, as described above. The use of the hydraulic drive enables substantially greater volumes of blood to be pumped, with greater efficiency, than pneumatic pump drive mechanisms that are commonly used in other cardiac assist pumps known in the art.

It will be appreciated that in preferred embodiments of the present invention, as described above, the blood being pumped remains entirely inside the cannula and in the first chamber of the fluid reservoir connected thereto, without circulating substantially outside the body. Preferably, the cannula and fluid reservoir are disposable, intended for a single use, so as to reduce the likelihood of infection.

In preferred embodiments of the present invention, the cannula is capable of pumping at least 50 cc, and preferably up to 80 cc of blood, in each stroke of the pulsatile drive unit. It will be appreciated, however, that depending on clinical requirements, the cardiac assist pump may be adjusted to pump a smaller volume in each stroke, for example 20 cc. The pulsatile drive unit is preferably operated substantially at the rate of the human heart beat, and adjusted so that adequate perfusion of the arterial system is maintained. The drive is preferably synchroniz with the heart beat, so as to draw blood into the lumen of the cannula during systole and eject the blood into the aorta during diastole.

Alternatively, the drive may be counter-synchronized, so as to draw blood into the lumen during diastole and eject it during systole, or the drive may be operated asynchronously, independent of the heart beat.

In preferred embodiments of the present invention, the cannula comprises a flexible, resilient tube having a diameter in the range of 15–30 French (5–10 mm). It is preferably inserted percutaneously through the femoral artery, into the aorta and then through the aortic valve into the left ventricle of the heart. Alternatively, the cannula may be inserted elsewhere into the arterial system through a suitable suraical incision.

In some preferred embodiments of the present invention, the at least one intake valve of the internal lumen of the cannula comprises a one-way mechanical flap valve or leaflet valve, as are known in the art. The at least one intake valve may comprise either an axial opening or one or more radial openings.

In some preferred embodiments of the present invention, the one or more outlet valves similarly comprise mechanical flap valves, which open radially outward when the pressure inside the lumen of the cannula increases, and close substantially flush with the outer surface of the cannula when the pressure inside the lumen is reduced.

In other preferred embodiments of the present invention, the cannula contains a rotatable intier sleeve, inside the outer sheath and radially enclosing the lumen. Preferably the sleeve extends along at least the portion of the length of the cannula along which the outlet valves are disposed. Each of the one or more outlet valves comprises a first opening in the inner sleeve and a corresponding second opening in the outer sheath. To open the outlet valve, the first and second openings are aligned, by suitably rotating the sleeve relative to the sheath. To close the valve, the sleeve is counter-rotated, so as to disalin the first and second openings.

Preferably, the sleeve is constructed so that blood flowing into the lumen causes a torque to be exerted on the sleeve, so that the sleeve rotates and the outlet valves are closed. When the direction of flow of the blood in the lumen is reversed. the sleeve rotates back to its previous orientation, in which the outlet valves are open, and the blood can flow out. Preferably the sleeve includes small wings or rotor blades fixed to its inner surface, for the purpose of converting the force of the blood flow into the torque exerted on the sleeve.

Alternatively, an externally-driven mechanical rotation device is coupled to the sleeve and/or the sheath so as to effect the desired relative rotation to open and close the one or more outlet valves.

In preferred embodiments of the present invention in which the cannula includes the rotatable inner sleeve, the at least one intake valve may comprise a mechanical flap or leaflet valve, as described above. Alternatively, the intake valve may comprise first and second openings, similar in function to the first and second openings of the outlet valves, except that when the first and second openings of the outlet valves are aligned, those of the inlet valve are disaligned, and vice-versa.

In other preferred embodiments of the present invention, the cannula contains a sliding element, held inside the lumen, adjacent to the distal end thereof, in such a manner that the sliding element can slide axially along the lumen but cannot rotate therein. The sliding element includes radial and axial openings through which blood can flow. The cannula further includes an axial opening, serving as an intake valve into the lumen, adjacent to the cannula's distal end, and one or more radial openings, serving as outlet valves from the lumen, along the length of the cannula proximal to the intake valve.

When the pressure inside the lumen is increased, the sliding element slides in the distal direction, thereby engaging and substantially closing the axial (intake) opening. When the sliding element is in this position, the radial openings of the sliding element are aligned with the radial openings in the cannula, so that blood may flow out of the lumen.

When the pressure inside the lumen is reversed, i.e., reduced to a negative pressure relative to the blood pressure outside the lumen, the sliding element slides proximally, away from the distal end of the cannula so that blood may flow into the lumen through the reopened axial openings of the cannula and the sliding element. In the proximal position, the radial openings of the sliding element are disaligned with the radial openings in the cannula, so that the outlet valves are effectively closed.

Alternatively, in other preferred embodiments of the present invention, which operate similarly to those just described, the cannula includes one or more radial intake openings, to serve as intake valves in place of the axial opening described above. The sliding element similarly includes radial intake openings, in place of the axial openings described above. When the pressure inside the lumen is reversed, i.e., reduced to a negative pressure relative to the blood pressure outside the lumen, the radial intake openings in the sliding element align with the radial intake openings in the lumen, so that blood may flow into the lumen. When the pressure inside the lumen is increased, the intake valves close, and the outlet valves open, as described above.

In still other preferred embodiments of the present invention, the outlet valves of the cannula comprise radial openings along the length thereof, which are covered and closed by a flexible, elastic outer sheath, preferably made of biocompatible rubber. The sheath is preferably held in place by a squeeze ring along a portion of its length. The at least one intake valve may comprise a mechanical flap, leaflet or other valve type described above or otherwise known in the art.

Alternatively, the at least one intake valve may similarly comprise a flexible, elastic inner sheath and operate in a manner similar to the outlet valves, as will be described below.

Normally, the elasticity of the outer sheath covering the outlet valves causes it to cling radially to the outer surface of the cannula, thereby closing the outlet valves. When the pressure inside the lumen of the cannula is increased, however, the pressure of the blood exerts an outward force on the sheath through the radial openings. This force causes the sheath to stretch outwards, allowing the blood to flow out of the lumen.

There is therefore provided, in accordance with a preferred embodiment of the present invention, a cardiac assist pump, including:

a cannula, including an outer sheath, which defines and encloses a lumen therein, the cannula having a distal end and a proximal end, wherein the cannula is inserted through the aorta of a subject so that the distal end is inside a ventricle of the heart of the subject;

at least one intake valve, adjacent to the distal end of the cannula, through which blood enters the lumen from the ventricle;

at least one outlet vaive, disposed radially along the sheath of the cannula, through which blood exits the lumen into the aorta;

a fluid reservoir, having a variable fluid volume, connected to the proximal end of the cannula, such that blood may flow between the lumen and the reservoir; and a pump drive, coupled to the fluid reservoir and controlling the fluid volume in said reservoir, wherein the pump drive alternately increases and decreases the fluid volume in the reservoir to produce a pulsatile pumping action of blood through the cannula.

Preferably, the reservoir has a minimum and a maximum volume, the difference therebetween defining a reservoir stroke volume, wherein the cardiac assist pump has a stroke volume substantially defined by the stroke volume of the fluid reservoir. Preferably, the pump has a maximum stroke volume or at least 50 cc, and more preferably, approximately 80 cc.

Preferably, the pump drive is hydraulically coupled to the fluid reservoir and is synchronized with the beating or the heart.

Preferably, the intake and outlet valves include at least one one-way valve. Additionally or alternatively, the intake and outlet valves include at least one mechanical flap valve, and/or the intake valve includes a leaflet valve.

Additionally or alternatively, the pump includes a rotatable inner sleeve, situated within the lumen, wherein rotation of the inner sleeve relative to the sheath opens and shuts at least one of the intake and outlet valves. Preferably, at least one of the intake and outlet valves includes a first radial opening in the sheath and a second, corresponding radial opening in the inner sleeve, wherein rotation of the inner sleeve relative to the sheath causes the at least one valve to open by bringing the respective first and second radial openings substantially into mutual alignment. Preferably, a torque-coupling device is coupled to the inner sleeve, which device preferably includes winglets fixed to the sleeve and causes the inner sleeve to rotate in response to blood flow in the lumen.

Alternatively or additionally, the pump includes an inner sliding element, situated within the lumen, which moves axially inside the lumen to alternately open and close the intake and outlet valves. Preferably, at least one of the intake and outlet valves includes a first radial opening in the sheath and a second, corresponding radial opening in the inner sliding element, and axial movement of the sliding element in the lumen causes the at least one valve to open by bringing the respective first and second radial openings thereof substantially into mutual alignment.

Alternatively or additionally the at least one intake valve includes an axial opening in the cannula, and the inner sliding element moves axially away from the axial opening in the cannula to open the intake valve.

Further alternatively or additionally, the pump includes an elastic outer sleeve, which clings elastically to an outer, radial surface of the cannula to close the outlet valves, wherein the elastic outer sleeve stretches outward in response to a pressure of the blood inside the cannula, thereby opening the outlet valves.

Moreover, alternatively or additionally, the pump includes an elastic inner sleeve, which clings elastically to an inner, radial surface of the cannula to close the intake valves, wherein when pressure of the blood inside the cannula is reduced, the elastic inner sleeve deforms inward in response to pressure of the blood outside the cannula, thereby opening the intake valves.

There is further provided, in accordance with a preferred embodiment of the present invention, a method for augmenting the blood output of the heart, including:

connecting a cannula, having distal and proximal ends and haing intake and outlet valves, to a fluid reservoir at the proximal end of the cannula;

inserting the cannula through an artery, so that the distal end of the cannula is inside the left ventricle of the heart;

drawing blood from the ventricle, through the intake valve of the cannula and into the fluid reservoir, by reducing a fluid pressure in the reservoir; and ejecting the blood from the reservoir through the outlet valve of the cannula and into the artery, by increasing the fluid pressure in the reservoir.

Preferably, drawing blood and ejecting blood are performed repeatedly, in alternation, wherein in each alternation, between 20 and 80 cc of blood are drawn and ejected. Preferably drawing and ejecting blood include applying hydraulic forces to the reservoir.

Preferably, the method includes sensing a heart beat signal, wherein drawing blood and ejecting blood comprise drawing and injecting blood in synchrony with the heart beat, wherein blood is drawn either during systole or during diastole.

Preferably, this method is carried out using a cardiac assist pump as described above.

There is further provided, in accordance with a preferred embodiment of the present invention, a one-way valve for use in a heart-assist device, which valve includes:

an outer sheath, defining an enclosing a lumen therein, and including a first radial opening;

an inner sleeve, rotatably held inside the outer sheath, and including a second radial opening, which is alignable with the first radial opening by rotation of the sleeve, such that when the first and second radial openings are mutually aligned, the valve is open; and a torque coupling device, coupled to the inner sleeve, wherein in response to flow of a fluid in the lumen in a first flow direction, the torque coupling device causes the sleeve to rotate in a first rotational direction, thereby altering the alignment of the first and second radial openings.

Preferably, in response to flow of the fluid in the lumen in a second flow direction, generally opposite to the first flow direction, the torque coupling device causes the sleeve to rotate in a direction opposite to the first rotational direction. Preferably, rotation of the sleeve in the first rotational direction causes the valve to open, and rotation of the sleeve in the opposite direction causes the valve to close.

Preferably, the torque coupling device includes winglets, fixed to the sleeve.

There is also provided, in accordance with a preferred embodiment of the present invention, a one-way valve assembly, including an intake valve and an outlet valve, for use in a heart-assist-device, which assembly includes:

an outer sheath, defining and enclosing a lumen therein and including a first intake opening and a first outlet opening; and an inner sliding element, held inside the lumen and axially movable therein, and including a second intake opening and a second outlet opening, respectively alienable with the first intake opening and the first outlet opening by axial movement of the sliding element, such that when the sliding element is in a first axial position, the first and second intake openings are aligned, so that the intake valve is open, and when the sliding element is in a second axial position, the first and second outlet openings are aligned, so that the outlet valve is open, wherein in response to changes of a fluid pressure inside the lumen, the inner sliding element moves axially in the sheath between the first and second axial positions.

Preferably, for any position of the sliding element intermediate the first and second axial positions, no more than one of the intake and outlet valves is open.

Preferably, in response to an increase of the fluid pressure inside the lumen, the inner sliding element moves to the second axial position, thereby opening the outlet valve, and in response to a decrease of the fluid pressure inside the lumen, the inner sliding element moves to the first axial position, thereby opening the intake valve.

There is additionally provided, in accordance with a preferred embodiment of the present invention, a one-way valve for use in a heart-assist device, which valve includes:

an outer sheath, defining and enclosing a lumen therein, and including a radial opening; and an elastic outer sleeve, which clings elastically to an outer, radial surface of the sheath to cover the radial opening, thereby closing the valve, wherein in response to an increase of a fluid pressure inside the lumen, the outer sleeve stretches outward, thereby opening the valve.

Moreover, in accordance with another preferred embodiment of the present invention, there is provided a one-way valve for use in a heart-assist device, said valve including:

an outer sheath, defining and enclosing a lumen therein, and including a radial opening; and an elastic inner sleeve, which clings elastically to an inner, radial surface of the sheath to cover the radial opening, thereby closing the valve, wherein in response to a decrease of a fluid pressure inside the lumen, the inner sleeve deforms inward, thereby opening the valve.

Preferably, such one-way valves including an elastic sleeve also include a retaining ring, circumferentially engaging a portion of the sleeve, which ring holds the sleeve in place relative to the sheath.

The present invention will be more fully understood from the following detailed description of the preferred embodiments thereof, taken together with the drawings in which:

DETAILED DESCRIPTION OF PREFERRED EMBODIMENTS

Figure 1:
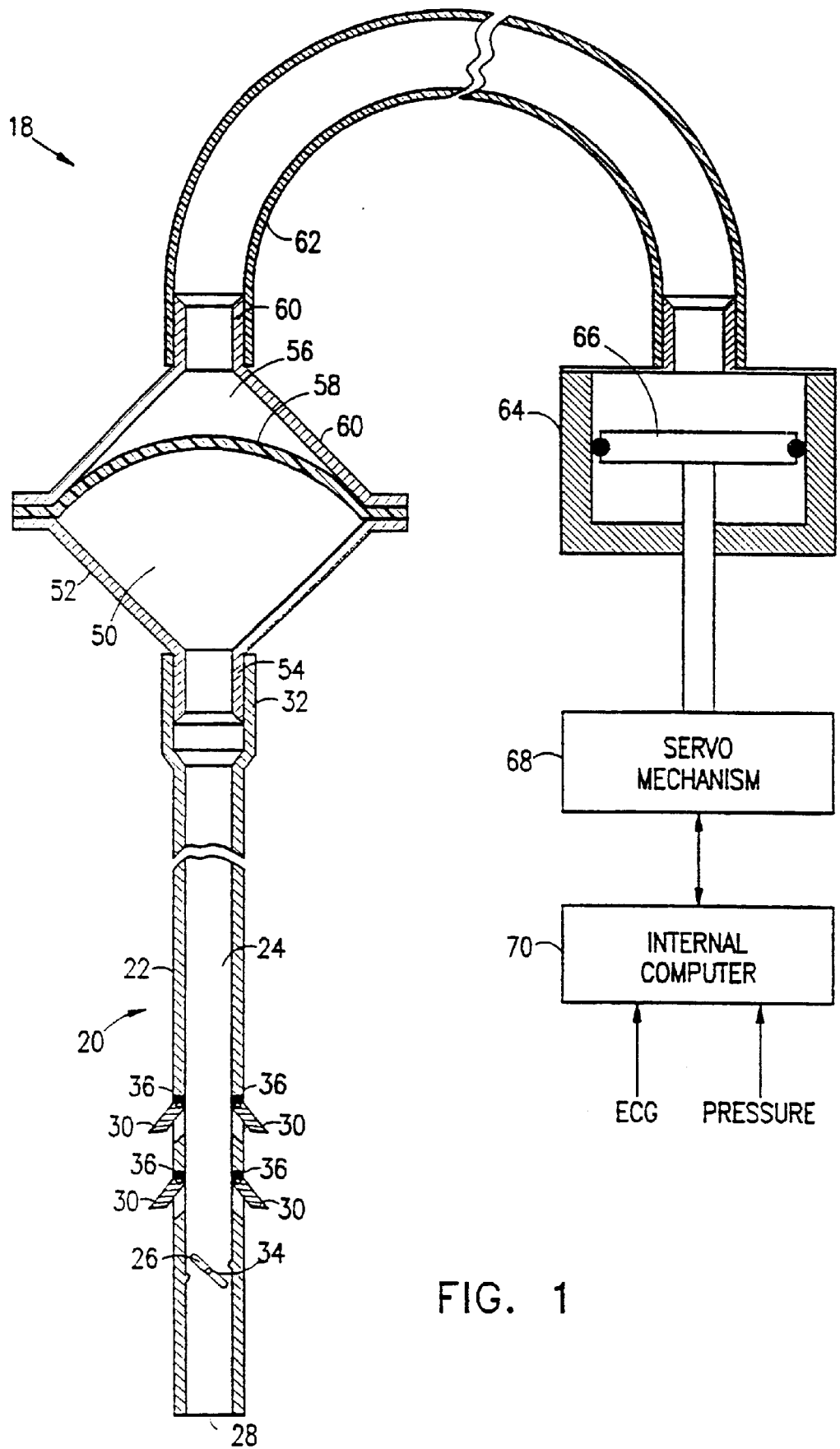
FIG. 1 is a schematic, sectional representation of a cardiac assist pump, in accordance with a preferred embodiment of the present invention.

Reference is now made to FIG. 1, which is a schematic, sectional representation of a cardiac assist pump system 18, in accordance with a preferred embodiment of the present invention. The system comprises an intra-aortic cannula 20, having an outer sheath 22, which defines and encloses an inner lumen 24. Preferably cannula 20 has a diameter in the range of 15–30 French (5–10 mm) and is made of flexible, resilient material, for example, polyurethane reinforced with stainless steel wire, so that it may be inserted into and passed through major arteries of tile human body. Cannula 20 further includes an intake valve 26, preferably axially disposed, adjacent to its distal end 28, and one or more outlet valves 30, radially disposed along sheath 22 of the cannula. The intake and outlet valves are preferably made of stainless steel or stiff plastic material, such as polycarbonate, or other suitable materials known in the art.

Intake valve 26 and outlet valves 30 are preferably one-way valves, so that blood may flow into and out of cannula 20 substantially only in a single direction: entering through intake valve 26 and exiting through outlet valves 30 (corresponding to the direction of blood flow in the body, as will be described below). In the preferred embodiment of the present invention shown in FIG. 1, the intake and outlet valves comprise mechanical flap valves, which rotate about respective hinges 34 and 36 to open and shut as desired. Although hinge 34 of intake valve 26 is shown to be located along a central axis of the valve, it may similarly be located at one side of the valve, like hinges 36 of outlet valves 30.

Alternatively, intake valve 26 may comprise any other suitable type of one-way valve, for example a leaflet valve.

Such leaflet valves are known in the art for use in heart-assist devices, as described, for example, in a PCT patent application entitled. "Method for Producing Heart Valves and Heart Valves Produced by the Method," filed on even date with the present application which is assigned to the assignee of the present invention and whose disclosure is incorporated herein by reference.

In other preferred embodiments of the present invention, as will be described below, other types of intake and outlet valves may similarly be used.

Figure 2A:
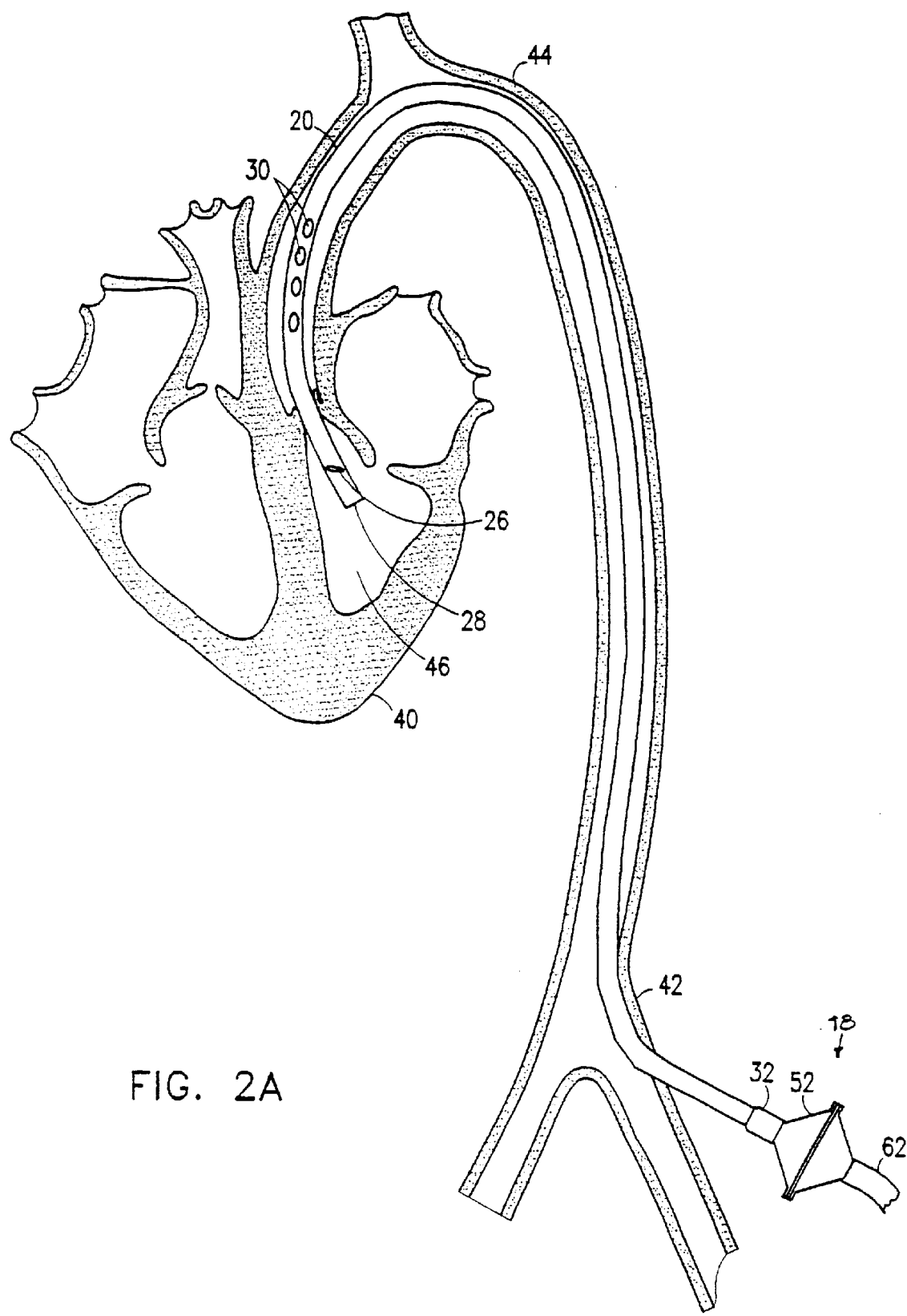
FIG. 2A is a schematic representation of a cannula in accordance with a preferred embodiment of the present invention, illustrating the insertion of the cannula into the heart.

FIG. 2A shows, schematically, the use of cannula 20 in a human heart 40. Preferably the cannula is inserted percutaneously, through an incision into a peripheral artery 42, for example the femoral artery, and passed upstream through aorta 44 into left ventricle 46 of heart 40. The method of insertion is substantially similar to methods for insertion of other types of cardiac cannulae known in the art. The length of cannula 20 is preferably approximately 60 cm, which is generally sufficient so that when distal tip 28 is positioned in ventricle 46. proximal end 32 remains outside the body, adjacent to the incision. Alternatively, the cannula may be inserted surgically through a suitable incision elsewhere in the arterial system, and in such cases may be shorter than 60 cm, depending on the distance from the incision to the heart.

Once cannula 20 is in place, intake valve 26 is opened, and blood flows from ventricle 46 into lumen 24. Preferably outlet valves 30 are kept closed while the blood fills the lumen. Proximal end 32 may be temporarily opened, to vent out air or fluid that was inside cannula 20 before its insertion. Then intake valve 26 is closed and outlet valves 30 are opened, so that the blood may flow out of the lumen and into aorta 44.

As illustrated in FIG. 1, intake valve 26 and outlet valves 30 preferably open and shut in response to pressure exerted through pump system 18 to cannula 20, in the following manner. Proximal end 32 of cannula 20 is connected to a first chamber 50 of a fluid reservoir 52 through a first fluid port 54. Fluid reservoir 52 further includes a second chamber 56, which is separated from first chamber 50 by a flexible diaphragm 58. Diaphragm 58, which is preferably made of flexible polyurethane, deforms to alter the respective volumes of chambers 50 and 56, so as to substantially equalize the fluid pressures in the two chambers, but prevents mingling of the fluids in the first and second chambers.

Second chamber 56 preferably contains a substantially incompressible liquid, such as water or, alternatively, any other suitable fluid, such as normal saline solution. Chamber 56 is coupled via a second fluid port 60 through a tube 62 to a pump drive 64. A piston 66 in pump drive 64 moves alternatively up and down to correspondingly increase and decrease the fluid pressure in reservoir 52, thereby pumping blood out of and into lumen 24.

It will be appreciated that the maximum volume of blood that may be pumped in a single stroke of piston 66 is roughly determined by the volume of reservoir 50. Preferably this maximum single stroke pumping volume is at least 50 cc, and more preferably up to 80 cc, although piston 66 may also be operated with a shorter stroke to pump a smaller volume of blood if desired. Preferably, the stroke is adjusted so that when pump drive 64 is operated at or about the heart's natural rate, sufficient blood can be pumped to perfuse substantially all of the person's body.

It will further be appreciated that blood may enter cannula 20 and flow into first chamber 50 only up to diaphragm 58. No blood flows through tubing 62 or into pump drive 64.

Preferably, cannula 20 and reservoir 52 are disposable and made for single use only, to prevent transfer of infections and contamination.

Pump drive 64 is driven by a servo mechanism 68, under the control of an internal computer 70, which regulates the rate and stroke volume of piston 66. Preferably, computer 70 receives physiological signal inputs, such as ECG and blood pressure signals, and uses these signals in optimally controlling pump drive 64, preferably to drive piston 66 at the rate of the heart beat.

Preferably, computer 70 adjusts the delay of the piston stroke relative to the systolic stroke of the heart. This delay may be adjusted so that cannula 20 pumps blood out synchronously with the heart's systole; counter synchronously, during diastole; or at any suitable phase therebetween. Alternatively, the rate of piston 66 may be set to be independent of the heart rate, for example in order to maintain steady perfusion during arrhythmia or fibrillation.

Figure 2B:
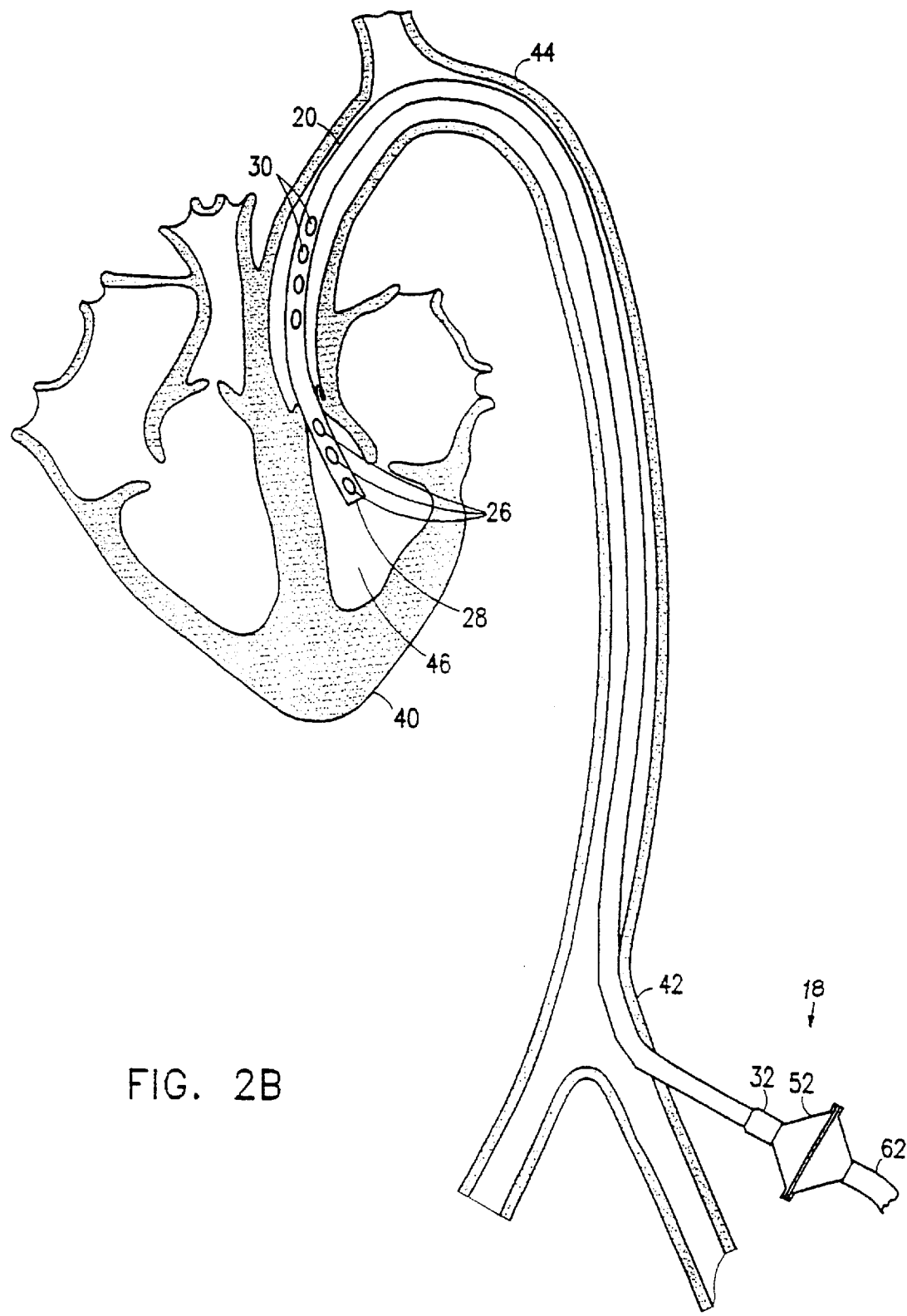
FIG. 2B is a schematic representation of a cannula in accordance with another preferred embodiment of the present invention, illustrating the insertion of the cannula into the heart.

FIG. 2B illustrates, schematically, an alternative preferred embodiment of the present invention, in which cannula 20, shown inserted into human heart 40, has a plurality of intake valves 26, radially disposed along the length of the cannula. Radial intake valves 26 may be flap valves, like valves 30 shown in FIG. 1 but opening inward, or one-way valves of other types described below or otherwise known in the art. It will be appreciated that the cannula shown in FIG. 2B functions in a substantially identical manner to that described above and illustrated in FIGS. 1 and 2A.

Figure 3:
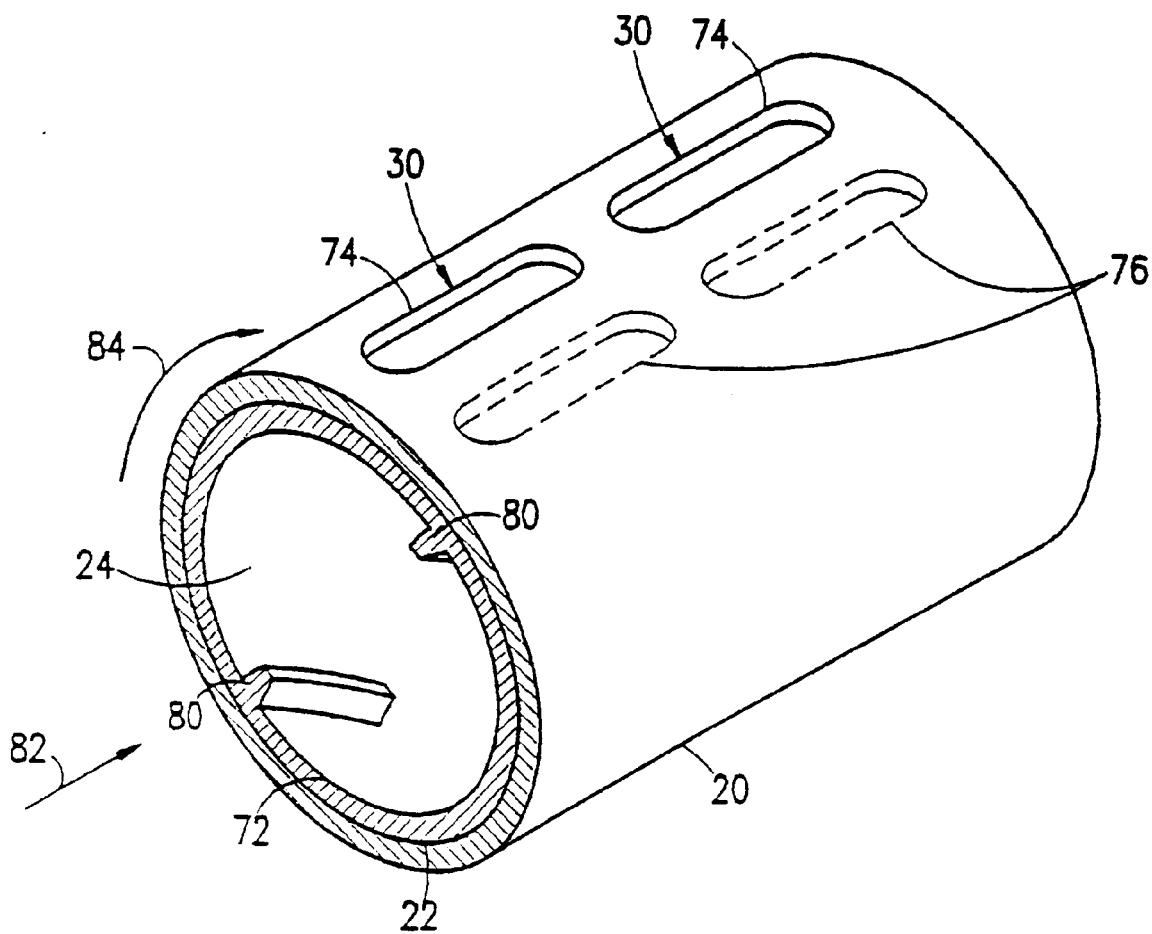
FIG. 3 is a schematic, sectional, isometric representation of a valve assembly in accordance with a preferred embodiment of the present invention.

FIG. 3 illustrates schematically an alternative construction of outlet valves 30, in accordance with another preferred embodiment of the present invention. As shown in FIG. 3, cannula 20 contains an inner sleeve 72, rotatably mounted inside outer sheath 22 and enclosing lumen 24. Inner sleeve 72 extends axially along at least the portion of cannula 20 including outlet valves 30. Each outlet valve 30 comprises an outer opening 74 in outer sheath 22 and an inner opening 76 in inner sleeve 72. To open outlet valves 30, inner sleeve 72 is rotated so that inner openings 76 are aligned with outer openings 74. When the inner and outer openings are disaligned, the valves are closed.

Preferably, a plurality of winglets 80 are fixed to the inner surface of sleeve 72 and cause the sleeve to rotate in response to blood flow through the lumen. When piston 66 is drawn back in pump drive 64, as shown in FIG. 1, blood will flow through lumen 24 substantially in the direction indicated in FIG. 3 by an arrow 82. The force of this flow against winglets 80 exerts a torque on sleeve 72, causing it to rotate in a clock-wise direction, as indicated in the figure by an arrow 84, thus closing outlet valves 30. When a desired volume of blood has been drawn into reservoir 50, piston 66 is pushed forward, so that blood flows in the lumen in the direction opposite to arrow 82. Sleeve 72 then rotates in the counterclockwise direction, so that outlet valves 30 open.

Alternatively, sleeve 72 or sheath 22 may be coupled proximally to a mechanical rotation drive, of any suitable type known in the art, so as to effect the desired relative rotation to open and close outlet valves 30.

In the preferred embodiment of the present invention utilizing the outlet valves shown in FIG. 3, intake valve 26 (not shown in the figure) may be a mechanical flap valve or leaflet valve, as described above. Alternatively, the intake valve may comprise a pair of alignable openings in sheath 22 and sleeve 72, which open and shut by the rotation of the sleeve relative to the sheath, in a manner similar to the operation of openings 74 and 76. The sheath and sleeve are constructed, however, so that when the pair of intake valve openings are aligned, to open intake valve 26, openings 74 and 76 are disaligned, to close outlet valves 30. Similarly, when the outlet valve openings are aligned, the intake valve openings are disaligned, and thus shut.

Figure 4A:
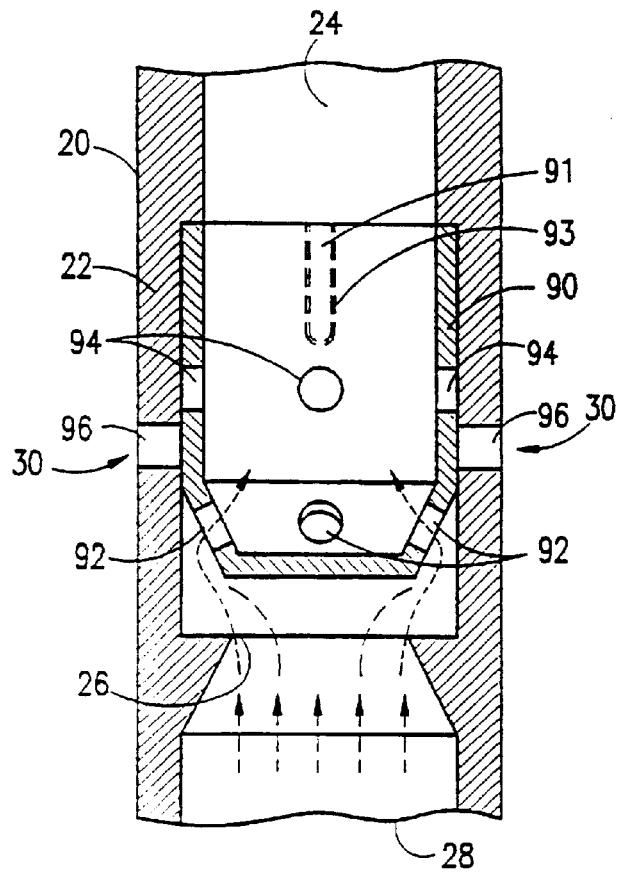
FIG. 4A is a sectional representation of a valve assembly in accordance with a preferred embodiment of the present invention, including intake and outlet valves, shown in a first position in which the intake valves are open and the outlet valves are closed.
Figure 4B:
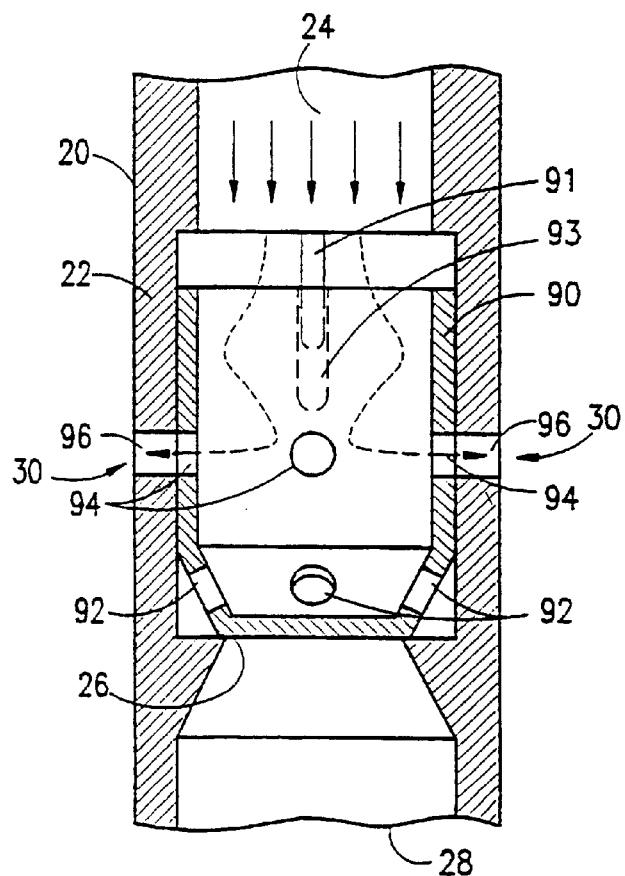
FIG. 4B is a sectional representation of the valve assembly of FIG. 4A shown in a second position in which the intake valves are closed and the outlet valves are open.

FIGS. 4A and 4B show still another preferred embodiment of the present invention, in which a sliding element 90 inside lumen 24 alternately opens and shuts intake valve 26 and outlet valves 30. Preferably, at least one axial tongue 91, fixed on the inner surface of cannula sheath 22, engages a matching groove 93 on the outer surface of sliding element 90, so that the sliding element may move up and down inside the lumen, but may not rotate about its axis.

In FIG. 4A, the pressure in lumen 24 has been reduced below the blood pressure at the proximal end of cannula 20, preferably by means of pump drive 64, as described above with reference to FIG. 1. The relatively greater pressure of the blood at the distal end of carmula 20, inside the left ventricle of the heart, forces sliding element 90 upward, opening intake valve 26. Blood flows into lumen 24 through valve 26, via sliding element front openings 92. Disalignment of sliding element side openings 94 with cannula radial openings 96 closes outlet valves 30.

In FIG. 4B, the pressure in lumen 24 is increased, forcing sliding element 90 downward and closing intake valve 26. Openings 94 and 96 are now mutually aligned, thus opening outlet valves 30, through which blood flows out into the aorta.

Figure 5A:
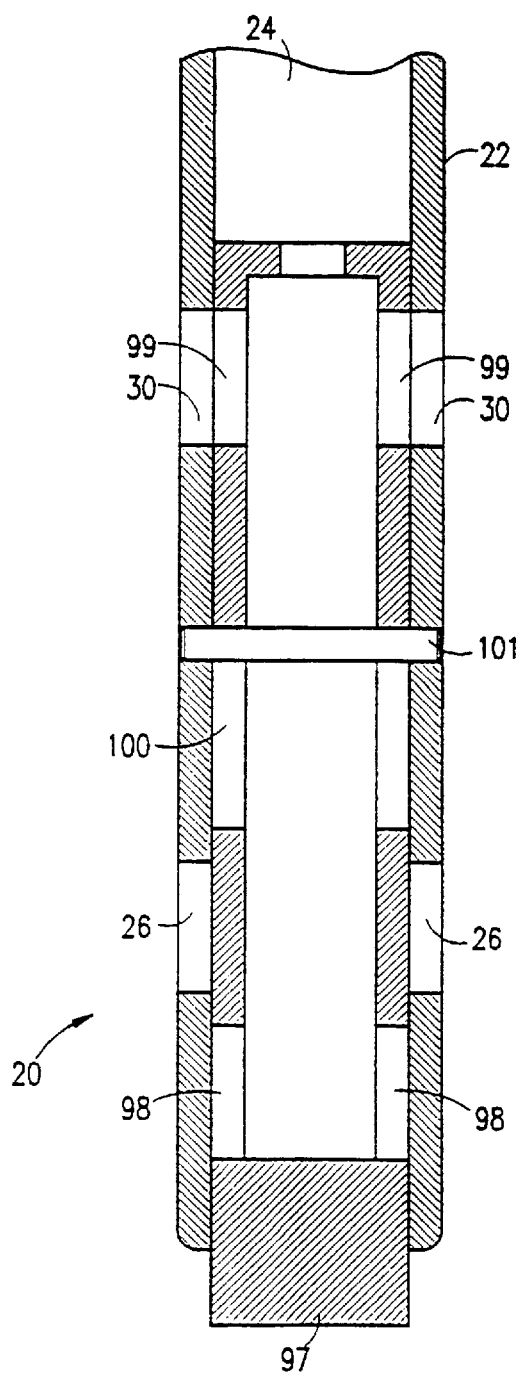
FIG. 5A is a sectional representation of a valve assembly in accordance with another preferred embodiment of the present invention, including intake and outlet valves, shown in a first position in which the intake valves are open and the outlet valves are closed.
Figure 5B:
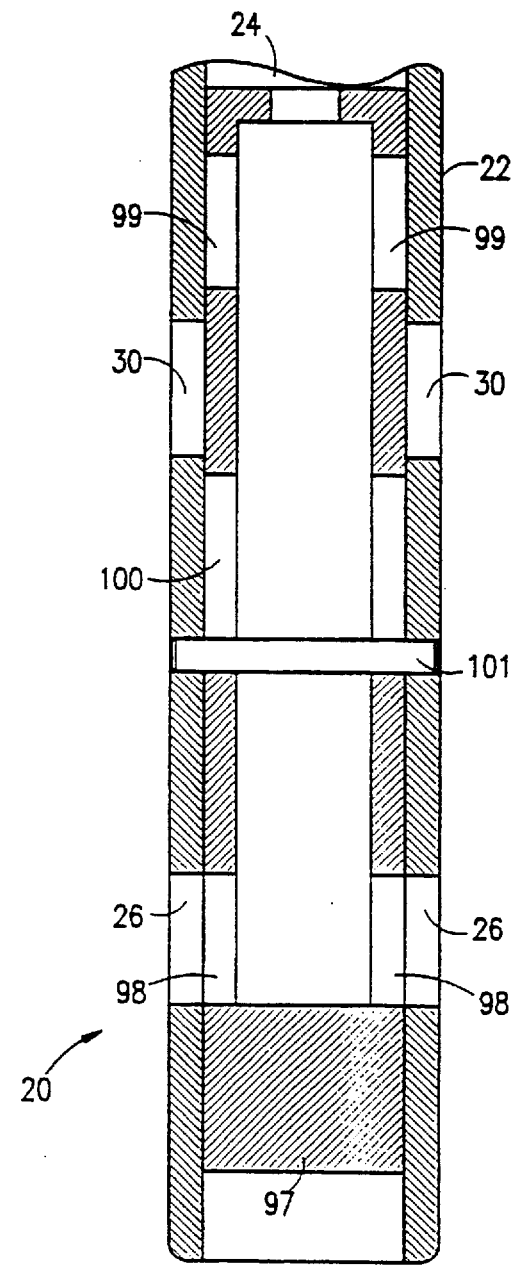
FIG. 5B is a sectional representation of the valve assembly of FIG. 5A, shown in a second position in which the intake valves are closed and the outlet valves are open.

FIGS. 5A and 5B illustrate another preferred embodiment of the present invention, substantially similar in operation to that shown in FIGS. 4A and 4B. In FIGS. 5A and 5B, however, intake valves 26 are radially disposed along sheath 22 of cannula 20, like outlet valves 30. A sliding stopper element 97 inside lumen 24 comprises at least two sets of radial openings: intake openings 98 and outlet openings 99. In FIG. 5A, increased pressure inside lumen 24 causes sliding element 97 to move downward, so that outlet openings 99 are aligned to open outlet valves 30. In FIG. 5B, reduced pressure in the lumen causes the sliding element to move upward, aligning, intake openings 98 with intake valves 26. A slot 100 in sliding element 97 engages a pin 101 fixed in sheath 22, so as to prevent rotation of the sliding element. Other methods of preventing rotation, as are known in the art, may also be used.

Figure 6A:
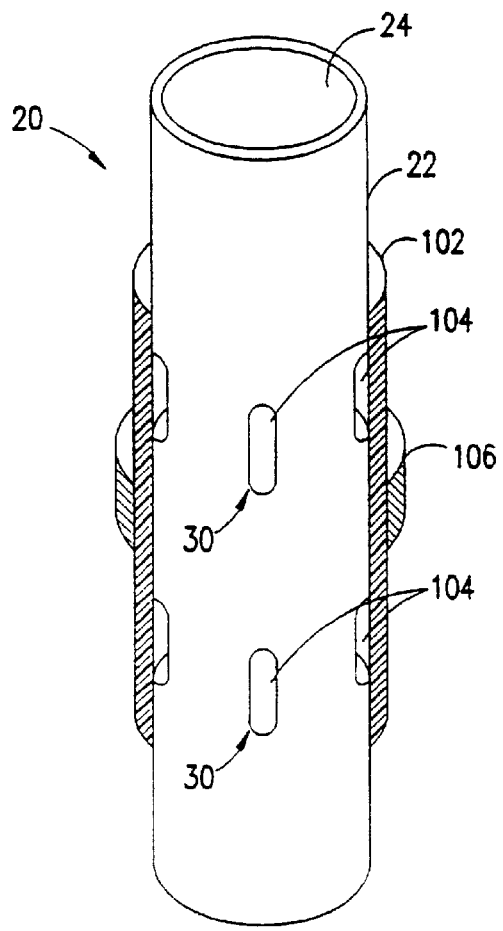
FIG. 6A is a schematic, partly sectional representation of a valve assembly in accordance with a preferred embodiment of the present invention, shown in a first position in which the valves are closed.
Figure 6B:
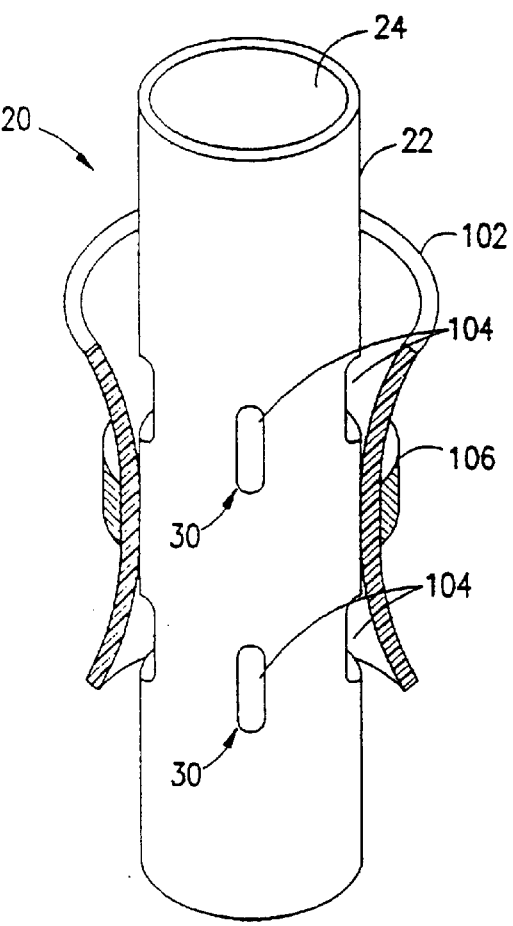
FIG. 6B is a schematic, partly sectional representation of the valve assembly of FIG. 6A, shown in a second position in which the valves are open.

FIGS. 6A and 6B illustrate still another preferred embodiment of the present invention, in which a flexible, elastic outer sleeve 102 covers and closes radial openings 104 in sheath 22 of cannula 20, which openings serve as outlet valves 30. Intake valve 26 (not shown in these figures) may comprise a mechanical flap valve or leaflet valve or any other suitable type described herein and/or known in the art. Sleeve 102, which is preferably made of latex silicone, or other biocompatible rubber, is preferably held in place by squeeze ring 106. Alternatively, sleeve 102 may be glued in place or otherwise secured.

In FIG. 6A, the pressure in lumen 24 has been reduced so that blood may be drawn in through the intake valve, as described above with reference to FIG. 1. The elasticity of sleeve 102 causes it to cling radially to the outer surface of cannula 20, so that outlet valves 30 remain closed.

In FIG. 6B, however, the pressure of the blood inside lumen 24 has been increased. This pressure exerts an outward force on sleeve 102 through openings 104, causing the sleeve to stretch outward, and thus opening outlet valves 30.

Figure 7A:
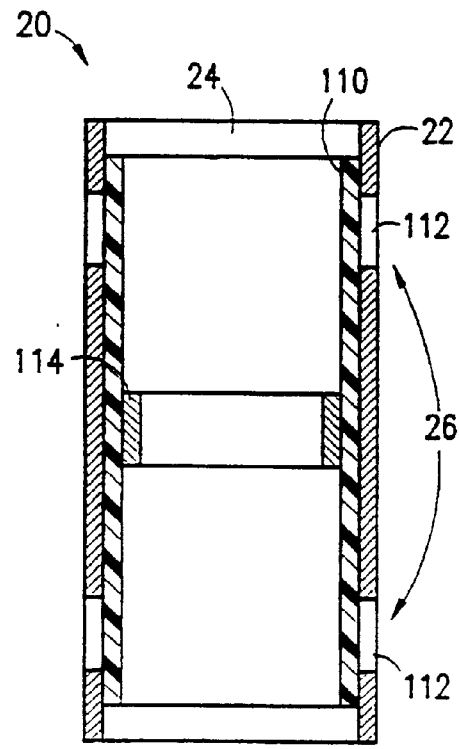
FIG. 7A is a schematic, sectional representation of another valve assembly in accordance with a preferred embodiment of the present invention, shown in a first position in which the valves are closed.
Figure 7B:
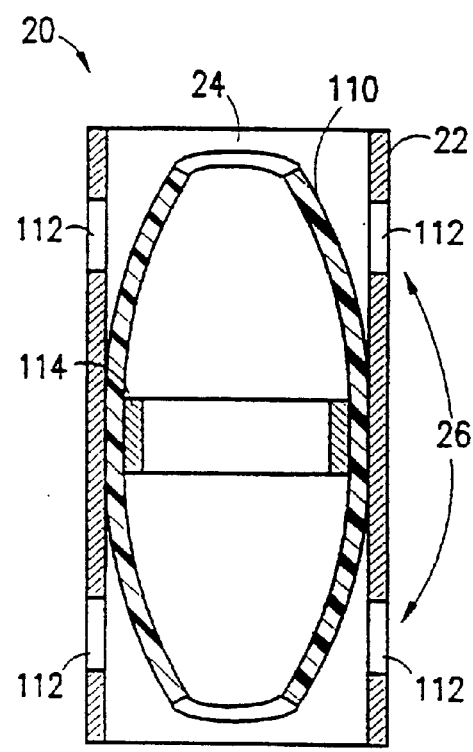
FIG. 7B is a schematic, sectional representation of the valve assembly of FIG. 7A, shown in a second position in which the valves are open.

As illustrated in FIGS. 7A and 7B, in a further preferred embodiment of the present invention, a flexible, resilient inner sleeve 110 covers and closes radial openings 112 in sheath 22 of cannula 20, which openings serve as intake valves 26. Sleeve 110 preferably comprises biocompatible rubber, as described above, and is preferably held in place by a substantially rigid expander ring 114. Alternatively, sleeve 110 may be glued in place or otherwise secured. When the pressure inside lumen 24 is greater than the blood pressure outside cannula 20, sleeve 110 is pressed outwards, closing valves 26, as shown in FIG. 7A. When the pressure inside the lumen is reduced, the pressure of the blood outside cannula 20, exerted through openings 112, causes sleeve 110 to deform inward, as shown in FIG. 7B, opening valves 26.

It will be appreciated that the preferred embodiments described above are cited by way of example, and the full scope of the invention is limited only by the claims.

We claim:

1. A cardiac assist pump, comprising:
    a cannula, comprising an outer sheath, which defines and encloses a lumen therein, said cannula having a distal end and a proximal end, wherein the cannula is adapted and configured so that it is capable of being inserted through the aorta of a subject so that the distal end is inside a ventricle of the heart of said subject;
    at least one intake valve, adjacent to the distal end of the cannula, through which blood enters the lumen from the ventricle;
    at least one outlet valve, disposed radially along the sheath of the cannula, through which blood exits the lumen into the aorta;
    a fluid reservoir having a variable fluid volume, connected to the proximal end of the cannula, such that blood may flow between the lumen and the reservoir; and
    a hydraulic pump, coupled to the fluid reservoir and applying hydraulic forces to the reservoir to control the fluid volume in said reservoir;
        wherein the pump mechanism alternately increases and decreases the fluid volume in the reservoir to produce a pulsatile pumpincg action of blood through the cannula.

2. A cardiac assist pump in accordance with claim 1, wherein the fluid reservoir has a minimum and a maximum fluid volume, the difference therebetween defining a reservoir stroke volume, and wherein the cardiac assist pump has a stroke volume defined by the reservoir stroke volume.

3. A cardiac assist pump in accordance with claim 2, having a maximum stroke volume of at least 50 cc.

4. A cardiac assist pump in accordance with claim 3, having a maximum stroke volume of approximately 80 cc.

5. A cardiac assist pump in accordance with claim 1, and including a controller that receives information regarding the beating of the heart and which controls the pump mechanism such that it is synchronized with the beating of the heart.

6. A cardiac assist pump in accordance with claim 1, wherein at least one of the intake and outlet valves comprise at least one one-way valve.

7. A cardiac assist pump in accordance with claim 1, wherein at least one of the intake and outlet valves comprise at least one mechanical flap valve.

8. A cardiac assist pump in accordance with claim 1 wherein the intake valve comprises a leaflet valve.

9. A cardiac assist pump in accordance with claim 1 and comprising a rotatable inner sleeve, wherein rotation of the inner sleeve relative to the sheath opens and shuts at least one of the intake and outlet valves.

10. A cardiac assist pump in accordance with claim 9, wherein the at least one of the intake and outlet valves comprises a first radial opening in the sheath and a second, corresponding radial opening in the inner sleeve, and wherein rotation of the inner sleeve relative to the sheath causes the at least one valve to open by bringing the respective first and second radial openings turnoff substantially into mutual alignment.

11. A cardiac assist pump in accordance with claim 9, and comprising a torque coupling device, coupled to the inner sleeve, which device generates torque in response to blood flow in the lumen, causing the inner sleeve to rotate.

12. A cardiac assist pump in accordance with claim 11, wherein the torque coupling device comprises winglets fixed to the sleeve.

13. A cardiac assist pump in accordance with claim 1, and comprising an inner axially slideable element situated within the lumen, wherein axial movement of the element inside the lumen is operative to alternatively open and close the intake and outlet valves at different axial positions of the inner element.

14. A cardiac assist pump in accordance with claim 13, wherein at least one of the intake and outlet valves comprises first radial opening in the sheath and a corresponding radial opening in the inner sliding element, and wherein the axial movement of the sliding element in the lumen causes the at least one valve to open by bringing the respective first and second radial openings thereof substantially into mutual alignment.

15. A cardiac assist pump in accordance with claim 13, wherein the at least one intake valve comprises an axial opening in the cannula, and wherein the inner sliding element moves axially away from the axial opening in the cannula to open the intake valve.

16. A cardiac assist pump in accordance with claim 1 and comprising an elastic inner sleeve, which clings elastically to an inner, radial surface of the cannula to close the intake valves.

17. A cardiac assist pump in accordance with claim 16, wherein the elastic inner sleeve deforms inward in response to a pressure of the blood outside the cannula, thereby opening the intake valves.

18. A cardiac assist pump in accordance with claim 1, and comprising an elastic outer sleeve, which clings elastically to an outer, radial surface of the cannula to close the outlet valves.

19. A cardiac assist pump in accordance with claim 18, wherein the elastic outer sleeve stretches outward in response to a pressure of the blood inside the cannula, thereby opening the outlet valves.

20. A cardiac assist pump in accordance with claim 1 wherein the reservoir is formed with a movable wall and wherein the hydraulic pump applies hydraulic pressure to the movable wall to cause the wall to move such that the volume of the reservoir is changed.

21. A cardiac assist pump in accordance with claim 20 wherein the movable wall is an elastic wall.

22. A method for augmenting the blood output of the heart, comprising:
    connecting a cannula, having distal and proximal ends and having intake and outlet valves, to a fluid reservoir at the proximal end of the cannula;
    inserting the cannula through an artery, so that the distal end of the cannula is inside the left ventricle of the heart;
    applying hydraulic forces to the reservoir such that:
        blood is drawn from the ventricle, through the intake valve of the cannula and into the fluid reservoir, by reducing a fluid pressure in said reservoir; and
        blood is elected from the reservoir through the outlet valve of the cannula and into the artery.

23. A method in accordance with claim 22, wherein drawing blood and ejecting blood are performed repeatedly, in alternation.

24. A method in accordance with claim 23 wherein in each alternation, between 20 and 80 cc of blood are drawn and ejected.

25. A method in accordance with claim 22, and comprising sensing a heart beat signal, wherein drawing blood and ejecting blood comprise drawing and injecting blood in response to the heart beat signal.

26. A method in accordance with claim 25, wherein drawing blood into the cannula comprises drawing blood during systole.

27. A method in accordance with claim 25, wherein drawing blood into the cannula comprises drawing blood during diastole.

28. A method in accordance with claim 22, wherein the reservoir comprises an movable wall and wherein applying hydraulic forces causes the movable wall to move such that the volume of the reservoir is changed.

29. A method in accordance with claim 22, wherein the resemble comprises an elastic wall and wherein applying hydraulic forces causes the elastic wall to move such that the volume of the reservoir is changed.

* * * * *